United States Patent
Maschke et al.

(10) Patent No.: US 8,219,183 B2
(45) Date of Patent: *Jul. 10, 2012

(54) APPARATUS FOR GENERATING SECTIONAL IMAGES OF TISSUE

(75) Inventors: Michael Maschke, Lonnerstadt (DE); Marcus Pfister, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 1295 days.

This patent is subject to a terminal disclaimer.

(21) Appl. No.: 11/977,110

(22) Filed: Oct. 23, 2007

(65) Prior Publication Data

US 2008/0101677 A1    May 1, 2008

(30) Foreign Application Priority Data

Oct. 27, 2006   (DE) .................. 10 2006 050 885

(51) Int. Cl.
*A61B 6/00* (2006.01)

(52) U.S. Cl. ........ 600/478; 600/473; 600/475; 600/476; 600/477

(58) Field of Classification Search ........... 600/473–478
See application file for complete search history.

(56) References Cited

U.S. PATENT DOCUMENTS

| | | | |
|---|---|---|---|
| 5,345,940 A | 9/1994 | Seward et al. | |
| 6,226,547 B1 | 5/2001 | Lockhart et al. | |
| 6,298,261 B1 | 10/2001 | Rex | |
| 6,377,048 B1 | 4/2002 | Golan et al. | |
| 6,600,319 B2 | 7/2003 | Golan | |
| 6,690,963 B2 | 2/2004 | Ben-Haim et al. | |
| 2005/0020925 A1 | 1/2005 | Kleen et al. | |
| 2006/0184049 A1* | 8/2006 | Tsujita | 600/478 |
| 2006/0211928 A1* | 9/2006 | Hull et al. | 600/317 |
| 2006/0241492 A1 | 10/2006 | Boese et al. | |
| 2006/0285791 A1* | 12/2006 | Piyevsky et al. | 385/25 |
| 2007/0038062 A1* | 2/2007 | Redel | 600/407 |
| 2007/0078500 A1* | 4/2007 | Ryan et al. | 607/88 |
| 2007/0265503 A1* | 11/2007 | Schlesinger et al. | 600/182 |
| 2008/0097225 A1* | 4/2008 | Tearney et al. | 600/478 |

FOREIGN PATENT DOCUMENTS

| | | |
|---|---|---|
| DE | 695 14 238 T2 | 2/1996 |
| DE | 198 52 441 A1 | 7/1999 |
| DE | 198 52 467 A1 | 7/1999 |
| DE | 103 23 217 A1 | 12/2004 |
| DE | 10 2005 012 699 A1 | 9/2006 |
| EP | 0 993 801 A1 | 4/2000 |
| EP | 1 034 738 B1 | 9/2000 |

OTHER PUBLICATIONS

Umar Mahmood et al., "Near Infrared Optical Imaging of Protease Activity for Tumor Detection", Radiology Dec. 1999, vol. 213, No. 3, pp. 866-870.

(Continued)

*Primary Examiner* — Brian Casler
*Assistant Examiner* — Amanda Lauritzen

(57) ABSTRACT

A generation of sectional images of tissue is provided. In this arrangement a first light-conducting fiber of a device for generating sectional tissue images according to the optical coherence tomography principle, which light-conducting fiber is rotatably accommodated within a catheter tube, is additionally connected to a device for generating light in a further wavelength range and for detecting fluorescent light. With its use sectional tissue images produced according to the optical coherence tomography principle can be superimposed with fluorescent images.

15 Claims, 3 Drawing Sheets

OTHER PUBLICATIONS

Grigorios Valassis, "Einfluβ der Photodynamischen Therapie auf die Neointimabildung vor and nach Stentimplantation in die Arteria femoralis des Hausschweines" Dissertation, Klinik Grosshadem, 2004, pp. 1-94.

R.J. Dickinson and R.I. Kitney "Miniature ultrasonic Probe construction for minimal access surgery" Phys. Med. Biol. 49 (2004), pp. 3527-3538.

H. V. Bibra et al., "Kontrastechokardiographie" Z.Kardiol 89: Suppl 1, pp. I/86-I/96, (2000).

Zhu et al., "Imager that combines near-infrared diffusive light and ultrasound", Optics Letters vol. 24, No. 15, Aug. 1, 1999, pp. 1050-1052.

* cited by examiner

APPARATUS FOR GENERATING SECTIONAL IMAGES OF TISSUE

CROSS REFERENCE TO RELATED APPLICATIONS

This application claims priority of German application No. 102006050885.8 DE filed Oct. 27, 2006, which is incorporated by reference herein in its entirety.

FIELD OF INVENTION

The invention relates to an apparatus for generating sectional images of tissue.

BACKGROUND OF INVENTION

An apparatus of this type is known for example from DE 10 2005 012 699 A1.

DE 103 23 217 A1 describes the production of high-resolution radial sectional images of tissue, for example, blood vessels. However, pathological changes in blood vessels, for example tumors, or deposits—plaques—found in blood vessels cannot always be identified by this means.

Umar Mahmood et al.: "Near Infrared Optical Imaging of Protease Activity for Tumor Detection", Radiology 213:3, 866-870 (1999) discloses fluorescent metabolic markers which bind specifically to specific pathogenic tissue regions. These pathogenic tissue regions may be, for example, tumors, inflammations, vessel portions affected with plaques, or other pathogenic foci. By exciting markers of this type with light of a suitable wavelength, pathogenic portions of tissue can be visualized and removed during a surgical operation.

The dissertation by Grigorios Valassis "Einfluss der photodynamischen Therapie auf die Neointimabbildung vor und nach der Stentimplantation in die Arteria femoralis des Hausschweins [Influence of photodynamic therapy on neointima imaging before and after stent implantation into the femoral artery of the domestic pig]", which was published in 2004, discloses that medicaments can be bound specifically to deposits present in veins and then released by irradiating with light to destroy the deposits.

SUMMARY OF INVENTION

The object of the present invention is to specify an apparatus for generating sectional images of tissue, with which apparatus healthy and pathogenic tissue portions may be displayed minimally invasively. According to a further aim of the invention, destruction or dissolution of pathogenic tissue is also to be achievable by this means.

This object is achieved by the independent claims. Advantageous embodiments of the invention emerge from the dependent claims.

According to the invention, a cycle-generating device is provided for the alternate operation of device I and device II or device I and device III.

Device I is a conventional optical coherence tomography device in which a catheter is provided. The catheter has a catheter tube in which a first light-conducting fiber is rotatably accommodated. Via the first light-conducting fiber, light is irradiated onto a tissue portion to be examined, and the light reflected from the tissue is transmitted to a receiver. The receiver evaluates the received first light signals in a conventional manner in such a way that a two-dimensional sectional tissue image orientated radially to the catheter can be produced therefrom according to the optical coherence tomography (OCT) principle.

According to the invention, device II for the coupling of secondary light or device III for receiving reflected secondary light is additionally connected to the first light-conducting fiber. The primary light used to produce sectional tissue images according to the optical coherence tomography principle differs in its first wavelength range from the second wavelength range of the secondary light. The first and second wavelength ranges advantageously do not overlap. The secondary light serves for example for the excitation of fluorophores, which bind specifically to pathogenic tissue portions. As a result of the excitation, the fluorophores generate a fluorescent light which may be emitted as secondary light and similarly detected via the first light-conducting fiber. According to the invention, the first light-conducting fiber is therefore additionally used for coupling the secondary light or for receiving reflected secondary light. This has the advantage that a conventional OCT catheter may be used. In particular, it is not absolutely essential to provide further light-conducting fibers in the catheter, which would increase the diameter thereof.

In order that both device I and device II or III may be used together with the first light-conducting fiber, according to a further feature of the invention a cycle-generating device is provided for the alternate operation of device I and device II or device I and device III. In this arrangement, a cycle of alternate operation is advantageously selected in such a way that sufficient information can be acquired per revolution of the first light-conducting fiber to generate a sectional tissue image and a fluorescent image.

Finally, according to a further feature of the invention an image-generating apparatus is provided to generate an overall image containing the image data of the sectional tissue images and of the tissue images. In the overall image in particular the position and arrangement of fluorophore markers in the tissue can be visualized and thus pathogenic tissue identified by simple means.

In the proposed invention it is possible in a minimally invasive manner to produce a differential representation of healthy and pathogenic tissue sections.

According to an especially advantageous embodiment of the invention, device II and device III are connected to the first light-conducting fiber, in which arrangement the cycle-generating device is designed for alternating operation of device I, device II and device III. In the proposed invention, therefore, the entire signal transmission to produce the sectional tissue images in accordance with the optical coherence tomography principle and to produce the tissue images generated by the secondary light, in particular fluorescent images, takes place via the first light-conducting fiber. In this case the cycle-generating device is designed in such a way that device I, II and III are driven alternately in such a way that device I receives the primary reflected light and device III the secondary reflected light induced by irradiation of the secondary light. The optical reciprocal effects with the irradiated tissue generated by the primary and the secondary light may therefore be observed and evaluated separately from one another.

According to an alternative embodiment of the invention, device II for coupling the secondary light is connected to a second light-conducting fiber accommodated within the catheter tube. In this case the thereto corresponding device III for receiving the reflected secondary light is connected to the first light-conducting fiber. According to a further alternative embodiment, device III for receiving is connected to a second light-conducting fiber accommodated within the catheter tube. In this case the thereto corresponding device II for coupling secondary light is connected to the first light-conducting fiber. The provision of a second light-conducting fiber makes it possible to operate device I, II or III connected to the first light-conducting fiber at a higher frequency.

In the case of provision of a second light-conducting fiber, the latter is advantageously connected to the first light-conducting fiber in such a way that the first light-conducting fiber is rotatable together with the second light-conducting fiber. This makes it possible to receive primary and secondary light reflected quasi-simultaneously with the same angle of rotation. Complicated correlation or registration of the data acquired to produce an entire image is unnecessary.

According to a further embodiment of the invention, a position-determining device is provided at the free end of the catheter tube for determining the position in a predetermined three-dimensional coordinate system. A position-determining device of this type advantageously comprises a plurality of position sensors which are advantageously disposed in the region of the free end. Catheters with the aforementioned position-determining device and processes for calculating the position of the free end of the catheter in a three-dimensional coordinate system are common knowledge according to the state of the art. In this regard reference is made by way of example to DE 198 52 441 A1 and DE 198 52 467 A1. Further position-determining devices are known for example from DE 695 14 238 T2 or EP 1 034 738 B1. Herein the position sensors are in the form of magnetic or electromagnetic transmitters or receivers which enter into an interaction with an external magnetic field. As a result of the interaction, in a three-dimensional coordinate system conclusions can be drawn regarding a position of the position sensors provided at the free end of the catheter. By this means it is possible to exactly follow a movement of the free end of the catheter tube, e.g. in a vessel. The proposed position sensors allow in particular an approximation of the mid-line of the vessel and an exact production of 3D images of the vessel therefrom.

According to a further embodiment of the invention, a deflecting means may be provided in the region of the free end. The deflecting means may comprise at least one and preferably a plurality of magnets. The magnets may be permanent magnets and/or electromagnets. In this arrangement, a magnetic field generated at least by two permanent magnets and/or electromagnets may have a different direction. With the proposed deflecting means it is possible, by applying suitable external magnetic fields, to deflect the—flexibly designed—free end of the catheter in a desired direction. This makes it easier to guide the catheter on a predetermined path within the vessel system.

According to a further embodiment of the invention, a line for passage of a fluid may be provided with its opening in the region of the free end of the catheter tube. The proposed line makes it possible for example to introduce fluids containing for example medicaments, fluorescent markers, tracers or the like.

The second wavelength range is advantageously selected in such a way that predetermined fluorophores are thereby excitable to generate fluorescent light. Fluorophores of this type may be, for example, a constituent of metabolic markers which bind specifically to specific pathogenic regions of the tissue. By excitation of the fluorophores, such pathogenic tissue regions may therefore become visible and thus be differentiated from healthy tissue regions. Furthermore it is possible to select the second wavelength range in such a way that optically activatable medicaments are released thereby.

According to a further advantageous embodiment of the invention, a superimposition device is provided for superimposing the sectional tissue image and the fluorescence image. By this means a region, for example within a sectional tissue image, in which fluorescent has been detected can be rendered identifiable. Such a range is an indication for example of pathogenic tissue portions. It is of course also possible conventionally to record a plurality of sectional tissue images by axial displacement of the catheter and to generate a 3-D image therefrom with which, for example, a vessel encircling the catheter can be displayed. Using the superimposition device proposed according to the invention, fluorescent tissue portions can also be visualized in a 3-D tissue image such as this.

According to a further embodiment of the invention, a position-calculating device is provided to calculate a position of the position-determining device in a three-dimensional coordinate system. This allows an exact correlation of the images obtained with other images obtained, for example, by radiographic methods. By this means it is also possible to produce exact three-dimensional images, for example of vessels, through which the catheter is moved.

Furthermore, a deflecting device may be provided for deflecting the deflecting means in accordance with a predetermined program. These are magnets known from the state of the art, with which the free end of the catheter is deflectable depending on the advancement length of the catheter in a predetermined direction.

Finally, a fluid-delivery device connectable to the line may be provided for the introduction of fluids. This may be a pump or the like, with which a predetermined quantity may be introduced, preferably at a predetermined rate, into the body via the line

BRIEF DESCRIPTION OF THE DRAWINGS

Exemplary embodiments of the invention are described in more detail below with reference to the drawings, in which.

DETAILED DESCRIPTION OF INVENTION

Figure 1:
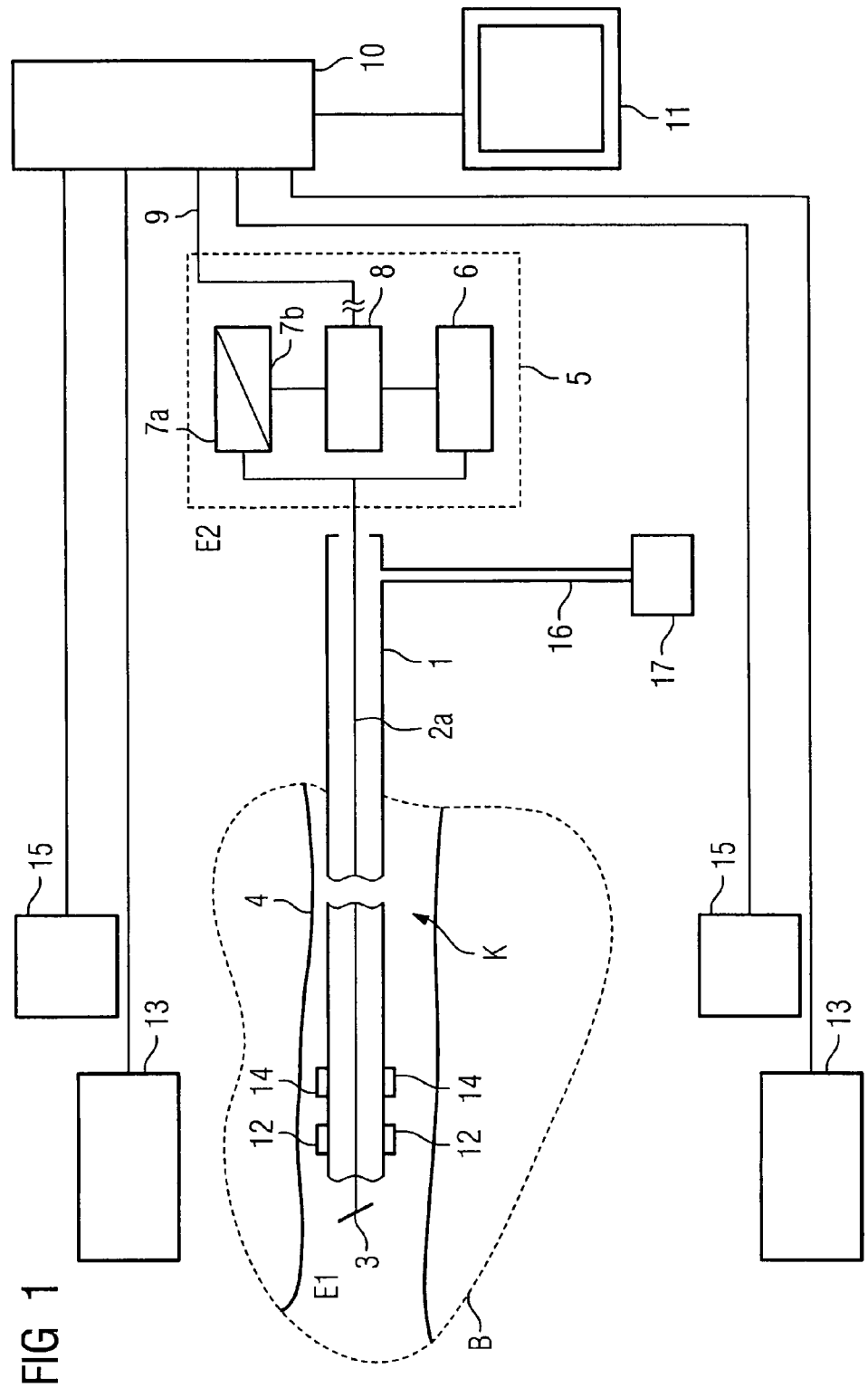
FIG. 1: shows a schematic block diagram of the essential components of a first apparatus.

FIG. 1 shows a schematic block diagram of a first apparatus. A catheter K has a flexible catheter tube and/or a catheter hose 1, in which a first light-conducting fiber 2a is rotatably accommodated. A reflecting means 3 for light, for example a mirror, is disposed at the free end E1 of the first light-conducting fiber 2a, with which reflecting means 3 primary and secondary light is irradiatable onto a vessel wall 4 and primary and secondary light reflected therefrom is detectable. Reference numeral 5 designates a rotational drive for rotating the first light-conducting fiber 2a. The first light-conducting fiber 2a is connected at its other end E2 opposite the free end E1 with an OCT device 6 for generating primary light and with a combined fluorescent light-generating device 7a and fluorescent light-detecting device 7b. For the alternating coupling of primary light and of secondary light generatable with the fluorescent light-generating device 7a, and for alternating detection of the reflected primary and secondary light, the OCT device 6 as well as the fluorescent light-generating device 7a and fluorescent light-detecting device 7b are connected to a cycle-generating device 8. The signals delivered with the OCT device 6 and with the fluorescent light-detecting device 7b for the purposes of image generation may for example be delivered to the cycle-generating device 8 and from there via separate channels with the use of a signal line 9 be transmitted to a computer 10 for the production of an image displayable on a monitor 11. At the free end E1 of the catheter tube 1, deflecting means 12 are attached which operate in conjunction with deflecting devices 13 provided outside a body schematically indicated with the reference key B. The deflecting devices 13 may be, for example, electromagnets the magnetic field strength and direction of which is controllable with the computer 10 in accordance with a predetermined program. The deflecting means 12 may for example be in the form of permanent magnets which, as a reaction to the magnetic field created with the deflecting device 13, cause deflection of the flexibly designed free end E1 of the catheter K in a desired direction.

The reference numerals 14 indicate position sensors. These may be electromagnetic coils of differing orientation, transponders or the like which cooperate with transmitting/receiving devices 15 in turn arranged outside the body B. With the transmitting/receiving devices 15, signals may be irradiated onto the position sensors 14 and/or signals radiated therefrom detected. From the detected signals, the determination of a position of the free end E1 of the catheter K is in turn possible with the use of conventional algorithms in a three-dimensional coordinate system determined for example by the arrangement of the transmitting/receiving devices 15.

The catheter tube 1 forms a line which is connected to a fluid-delivering device 17 via a hose 16. By this means fluorescent markers, medicaments and the like can be transported to an opening provided at the free end E1.

Figure 2:
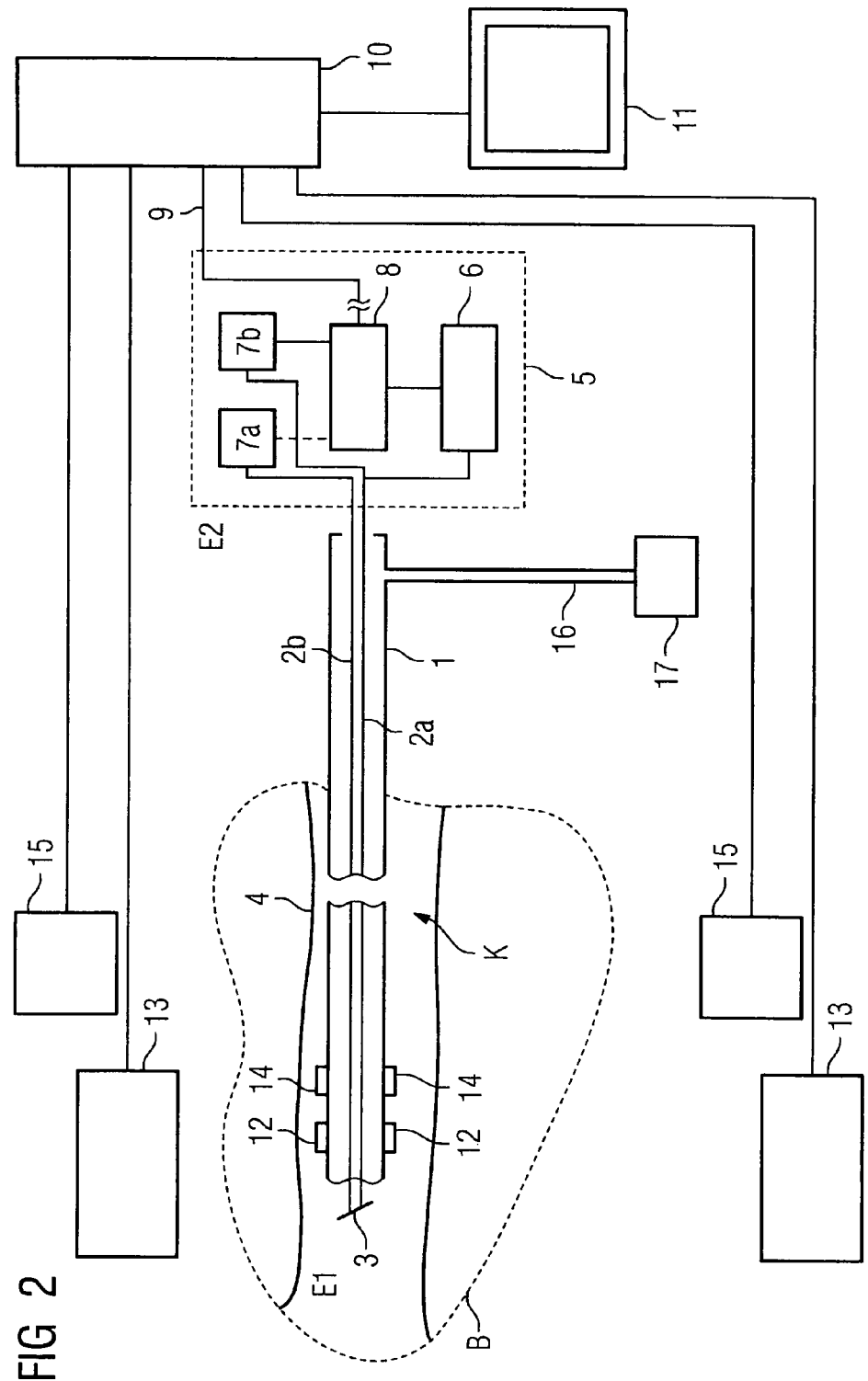
FIG. 2: shows a schematic block diagram of the essential components of a second apparatus.

FIG. 2 shows a second apparatus in another schematic block diagram. In this embodiment, a second light-conducting fiber 2b is provided in catheter tube 1 near to the first light-conducting fiber 2a. The first 2a and the second light-conducting fiber 2b are solidly connected to one another and jointly rotatable. The other end E2 of the first light-conducting fiber 2a is in turn connected to the OCT device 6. In a departure from the first apparatus shown in FIG. 1, here the other end E2 is connected only to the fluorescent light-detecting device 7b. To guarantee an alternating optical signal access to the first light-conducting fiber 2a, the fluorescent light-detecting device 7b and the OCT device 6 are in turn connected to the cycle-generating device 8. At the other end E2, the second light-conducting fiber 2b is connected to the fluorescent light-generating device 7a, which is here functionally separated from fluorescent light-detecting device 7b. The fluorescent light-generating device 7a may similarly be connected to the cycle-generating device 8. Instead of fluorescent light-detecting device 7b, it is of course also possible to connect fluorescent light-generating device 7a to the first light-conducting fiber 2a and fluorescent light-detecting device 7b to the second light-conducting fiber 2b.

Figure 3:
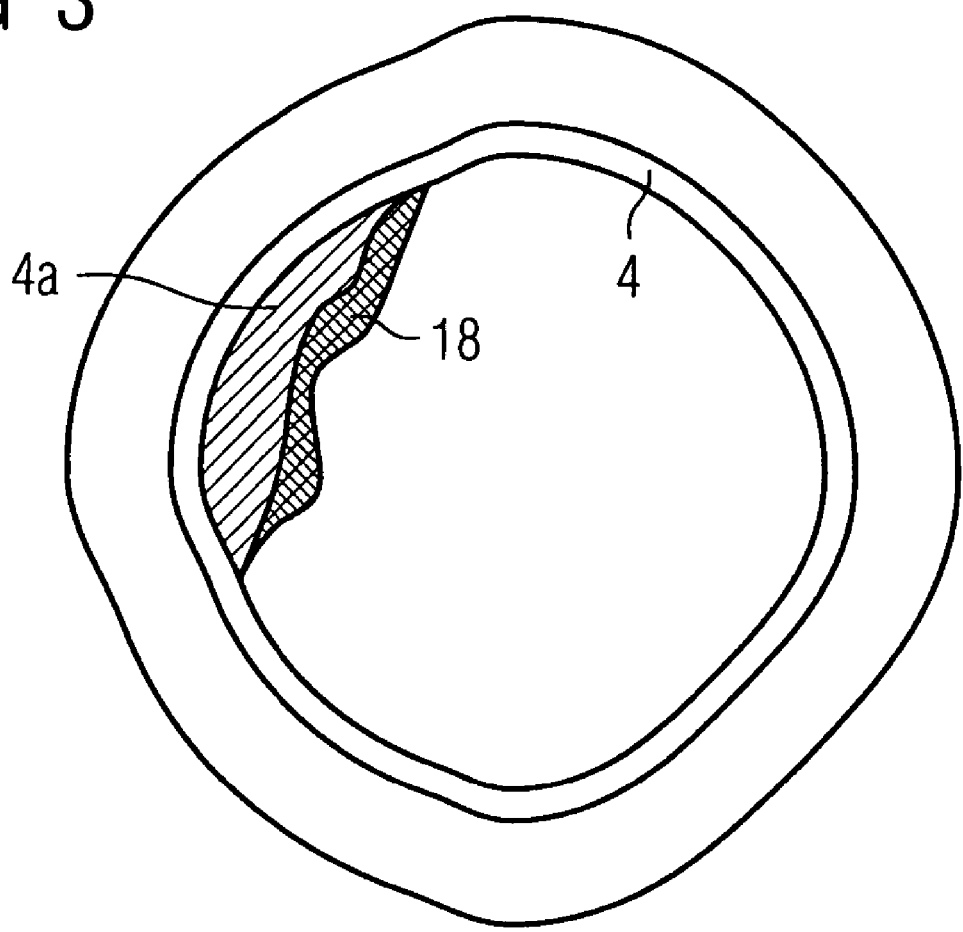
FIG. 3: shows a schematic representation of a superimposed image generated with the image-generating device.

FIG. 3 shows an overall image produced with the apparatus according to the invention. This is a sectional tissue image. A deposit 4a is present on the vessel wall 4. A fluorescent image 18 is superimposed on the sectional tissue image, which fluorescent image 18 additionally shows the position of the deposit 4a-determined pathogenic tissue portions.

The function of the device is as follows:

To produce sectional tissue images extending radially relative to the first light-conducting fiber 2a according to the optical coherence tomography principle, the first light-conducting fiber 2a is rotated, if appropriate together with the second light-conducting fiber 2b, by means of the rotating device 5. As a result of cooperation of the cycle-generating device 8 with the OCT device 6, primary light is irradiated cyclically onto the vessel wall 4 via the first light-conducting fiber 2a and primary light reflected therefrom is detected. As a result of this, a sectional tissue image can be produced due to the detected alternating effects of the primary light by means of the OCT device 6 in cooperation with a suitable image-generating software, which may be provided for example on the computer 10. However, on account of the cyclical operation of the OCT device 6, the image generating by this means is of course not a complete sectional tissue image, but only a sectional tissue image consisting of a plurality of sectors separated from one another by gaps. A complete sectional tissue image can be reconstructed from the sector-wise recorded sectional tissue image by means of suitable conventional image-reconstruction and/or interpolation algorithms. In place of a computerized reconstruction of the complete sectional tissue image, it is also possible to use primary light signals to generate the sectional tissue image, which primary light signals have been picked up over two or more rotations of the first light-conducting fiber 2a. In this arrangement, during the second rotation of the first light-conducting fiber 2a, the cycle selected for operation of the OCT device 6 may be offset relative to the cycle during the first rotation of the first light-conducting fiber 2a, with the result that overall image data may be picked up over the entire rotation range. A complete tissue layer image may also be produced by superimposing the signals acquired during the first and the second rotation of the first light-conducting fiber 2a.

In a similar way to the OCT device 6, the fluorescent light-detecting device 7b and—as in the case of the first apparatus shown in FIG. 1—the fluorescent light-generating device 7a may be driven by the cycle-generating device 8 in such a way that its operation does not distort the operation of the OCT device 6. In this way in particular during the downtimes of the OCT device 6 for the purposes of signal acquisition be connected to the first light-conducting fiber 2a. The fluorescence signals acquired thereby in dependence on the angle of rotation of the first light-conducting fiber 2a—as in accordance with the OCT method—may then be displayed with suitable false-color representation in the sectional tissue image to produce an overall image.

The invention claimed is:

1. An apparatus for generating sectional images of tissue, comprising:
    a catheter having a first light-conducting fiber rotatably accommodated within a catheter tube;
    a rotational drive device arranged to selectively rotate the first light-conducting fiber;
    a first device optically coupled to transmit primary light of a predetermined first wavelength range into the first light-conducting fiber and to receive reflected primary light transmitted via the first light-conducting fiber, the first device configured to generate sectional tissue images according to the optical coherence tomography principle;
    a second device optically coupled to transmit secondary light of a predetermined second wavelength range and a third device optically coupled to receive reflected secondary light and generate tissue images from the reflected secondary light, the second device or the third device being connected to the first light-conducting fiber;
    an image-generating device configured to generate an overall image containing the image data of the sectional tissue images and images of tissue, and a cycle-generating device electrically coupled to temporally alternate between an operation of the first device and an operation of the second device or the first device and third device, wherein the second wavelength range is selected such that predetermined fluorophores are thereby excitable to generate fluorescent light.

2. The apparatus as claimed in claim 1, wherein the second device and the third device are connected to the first light-conducting fiber, and wherein the cycle-generating device driving the first device, the second device and third device interchangeably such that the first device in each case receives the primary reflected light and the third device the secondary reflected light.

3. The apparatus as claimed in claim 1, wherein the second device is connected to a second light-conducting fiber accommodated within the catheter tube for a coupling the secondary light.

4. The apparatus as claimed in claim 1, wherein the third device is connected to a second light-conducting fiber accommodated within the catheter tube for the purposes of receiving.

5. The apparatus as claimed in claim 1, further comprises a position-determining device positioned at a free end of the catheter tube to determine the position in a predetermined three-dimensional coordinate system.

6. The apparatus as claimed in claim 5, wherein the position-determining device comprises a plurality of position sensors.

7. The apparatus as claimed in claim 1, wherein a deflector comprising at least one magnet is attached in the region of a free end of the catheter tube.

8. The apparatus as claimed in claim 1, further comprises a line in the catheter tube for passage of a fluid to a free end of the catheter tube.

9. The apparatus as claimed in claim 1, further comprises a superimposition device to superimpose the sectional tissue image and a fluorescent image generated from the fluorescent light.

10. The apparatus as claimed in claim 5, further comprises a position-calculating device to calculate a position of the position-determining device in a three-dimensional coordinate system.

11. The apparatus as claimed in claim 10, further comprises an apparatus to generate a three-dimensional image on the basis of the signals delivered by the position-calculating device.

12. The apparatus as claimed in claim 7, further comprises a deflecting device arranged to deflect the deflector in accordance with a predetermined program.

13. The apparatus as claimed in claim 8, further comprises a fluid-delivery device connectable to the line provided for the delivery of fluid.

14. An apparatus for generating sectional images of tissue, comprising:

a catheter having a first light-conducting fiber rotatably disposed within a catheter tube;

a rotational drive device arranged to selectively rotate the first light-conducting fiber;

a first device optically coupled to transmit primary light of a predetermined first wavelength range to the first light-conducting fiber and to receive reflected primary light transmitted via the first light-conducting fiber, the first device configured to generate sectional tissue images based on a principle of optical coherence tomography;

a second device optically coupled to transmit secondary light of a predetermined second wavelength range selected so that fluorophore markers delivered to the tissue in a fluid, which passes through a line in the catheter tube are excitable to generate fluorescent light in response to the secondary light based on a principle of fluorescence;

a third device optically coupled to receive the fluorescent light and generate a fluorescent image, the second device or the third device being optically coupled to the first light-conducting fiber;

a cycle-generating device electrically coupled to perform one of the following: 1) temporally alternate between an operation of the first device based on the principle of optical coherence tomography and an operation of the second device based on the principle of fluorescence; and 2) temporally alternate between an operation of the first device based on the principle of optical coherence tomography and an operation of the third device based on the principle of fluorescence; and an image-generating device configured to generate an overall image containing image data of the sectional tissue images and the fluorescence image.

15. The apparatus of claim 14, further comprising an image superimposition device configured to process a respective first section of the sectional tissue image and a respective first section of the fluorescent image acquired during at least a first revolution of the first light-conducting fiber, the image superimposition device further configured to process a respective second section of the sectional tissue image and a respective second section of the fluorescent image acquired during at least a second revolution of the first light-conducting fiber, wherein said respective first and second sections of the sectional tissue image and the fluorescent image acquired during said at least first revolution of the first light-conducting fiber comprise spatially-offset sections with respect to the respective first and second sections of the sectional tissue image and the fluorescent image acquired during said at least second revolution of the first light-conducting fiber, where the image superimposition device is configured to superimpose said spatially-offset sections to form the overall image.

* * * * *